United States Patent
Hyde et al.

(10) Patent No.: US 9,345,609 B2
(45) Date of Patent: May 24, 2016

(54) POSITION SENSING ACTIVE TORSO SUPPORT

(71) Applicants: Roderick A. Hyde, Redmond, WA (US);
Jordin T. Kare, Seattle, WA (US);
Dennis J. Rivet, Chesapeake, VA (US);
Lowell L. Wood, Jr., Bellevue, WA (US)

(72) Inventors: Roderick A. Hyde, Redmond, WA (US);
Jordin T. Kare, Seattle, WA (US);
Dennis J. Rivet, Chesapeake, VA (US);
Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 432 days.

(21) Appl. No.: 13/739,868

(22) Filed: Jan. 11, 2013

(65) Prior Publication Data

US 2014/0200496 A1 Jul. 17, 2014

(51) Int. Cl.
*A61F 5/02* (2006.01)
*A61F 5/32* (2006.01)

(52) U.S. Cl.
CPC .... *A61F 5/02* (2013.01); *A61F 5/32* (2013.01)

(58) Field of Classification Search
CPC combination set(s) only.
See application file for complete search history.

(56) References Cited

U.S. PATENT DOCUMENTS

| | | |
|---|---|---|
| 4,135,503 A | 1/1979 | Romano |
| 4,552,135 A | 11/1985 | Racz et al. |
| 4,605,582 A | 8/1986 | Sias et al. |
| 5,226,874 A | 7/1993 | Heinz et al. |
| 5,346,461 A | 9/1994 | Heinz et al. |
| 5,437,617 A | 8/1995 | Heinz et al. |
| 5,624,383 A | 4/1997 | Hazard et al. |
| 5,628,721 A | 5/1997 | Arnold et al. |
| 5,749,838 A | 5/1998 | Kline |
| RE35,940 E | 10/1998 | Heinz et al. |
| 5,827,209 A | 10/1998 | Gross |
| 6,007,459 A | 12/1999 | Burgess |
| 6,050,962 A | 4/2000 | Kramer et al. |
| 6,137,675 A | 10/2000 | Perkins |
| 6,331,170 B1 | 12/2001 | Ordway |
| 6,540,707 B1 | 4/2003 | Stark et al. |
| 6,746,413 B2 | 6/2004 | Reinecke et al. |
| 6,776,767 B2 | 8/2004 | Reinecke et al. |
| 6,974,432 B2 | 12/2005 | Reinecke et al. |
| 6,997,892 B2 | 2/2006 | Reinecke |
| 7,063,677 B1 | 6/2006 | Daggett |
| 7,070,571 B2 | 7/2006 | Kramer et al. |
| 7,074,201 B2 | 7/2006 | Reinecke et al. |
| 7,330,566 B2 | 2/2008 | Cutler |

(Continued)

FOREIGN PATENT DOCUMENTS

| | | |
|---|---|---|
| WO | WO 2008/150746 A1 | 12/2008 |
| WO | WO 2010/027689 A1 | 3/2010 |

OTHER PUBLICATIONS

PCT International Search Report; International App. No. PCT/US2013/075943; Apr. 3, 2014; pp. 1-3.

(Continued)

*Primary Examiner* — Ophelia A Hawthorne

(57) ABSTRACT

An active torso support includes multiple force applying elements for applying force to selected regions of a torso of a subject, to reduce or prevent injury or discomfort, under the control of control circuitry on the torso support. Target regions for application of force are selected by detecting the position of a landmark in or on the torso of the subject relative to a portion of the torso support, and selecting one or more force applying elements closest to the target region. Force can be applied according to spatial or temporal patterns, selected in response to user input or detected motion or activity of the subject. Related devices and methods are described.

30 Claims, 9 Drawing Sheets

(56) References Cited

U.S. PATENT DOCUMENTS

| | | |
|---|---|---|
| 7,413,554 B2 | 8/2008 | Kobayashi et al. |
| 7,416,537 B1 | 8/2008 | Stark et al. |
| 7,553,266 B2 | 6/2009 | Abdoli-Eramaki |
| 7,616,779 B2 | 11/2009 | Liao et al. |
| 7,628,766 B1 | 12/2009 | Kazerooni et al. |
| 7,654,972 B2 | 2/2010 | Alleyne |
| 7,728,839 B2 | 6/2010 | Yang et al. |
| 7,871,388 B2 | 1/2011 | Brown |
| 8,012,113 B2 | 9/2011 | Lee et al. |
| 8,025,632 B2 | 9/2011 | Einarsson |
| 8,074,559 B2 | 12/2011 | Altobelli et al. |
| 8,147,437 B2 | 4/2012 | Alleyne |
| 8,170,656 B2 | 5/2012 | Tan et al. |
| 8,177,733 B2 | 5/2012 | Ashihara et al. |
| 8,396,283 B2 | 3/2013 | Iihoshi et al. |
| 8,657,772 B2 | 2/2014 | Einarsson |
| 8,845,754 B2 * | 9/2014 | Streeter ............... A61F 2/68 602/13 |
| 8,870,970 B2 | 10/2014 | Altobelli et al. |
| 8,882,852 B2 | 11/2014 | Altobelli et al. |
| 8,928,484 B2 * | 1/2015 | Chang ............... A61B 5/0002 340/573.1 |
| 2001/0008955 A1 | 7/2001 | Garth |
| 2001/0020143 A1* | 9/2001 | Stark et al. ............ 602/13 |
| 2003/0135134 A1 | 7/2003 | Chase et al. |
| 2004/0003455 A1 | 1/2004 | Davidson |
| 2004/0077982 A1 | 4/2004 | Reinecke |
| 2005/0043660 A1 | 2/2005 | Stark et al. |
| 2005/0182287 A1 | 8/2005 | Becker |
| 2005/0197607 A1 | 9/2005 | Brown |
| 2006/0149179 A1 | 7/2006 | Alleyne |
| 2006/0161085 A1 | 7/2006 | Wikenheiser et al. |
| 2008/0039764 A1 | 2/2008 | Nordt, III et al. |
| 2009/0030359 A1 | 1/2009 | Wikenheiser et al. |
| 2009/0177131 A1 | 7/2009 | Dar et al. |
| 2009/0287109 A1 | 11/2009 | Ferren et al. |
| 2010/0075817 A1 | 3/2010 | Abdoli-Eramaki |
| 2010/0113995 A1 | 5/2010 | Alleyne |
| 2010/0198067 A1 | 8/2010 | Mahfouz et al. |
| 2010/0198124 A1 | 8/2010 | Bhugra |
| 2010/0256717 A1 | 10/2010 | Brown |
| 2011/0028875 A1 | 2/2011 | Martinez Ferro et al. |
| 2011/0034842 A1 | 2/2011 | Guldalian |
| 2011/0082393 A1 | 4/2011 | Bort |
| 2011/0213283 A1 | 9/2011 | Brown |
| 2011/0230806 A1 | 9/2011 | Lou et al. |
| 2011/0247321 A1 | 10/2011 | Streeter et al. |
| 2011/0301519 A1 | 12/2011 | Lan et al. |
| 2012/0116252 A1 | 5/2012 | Newman et al. |
| 2012/0116276 A1 | 5/2012 | Martinez Ferro et al. |
| 2012/0184887 A1 | 7/2012 | Wynne et al. |
| 2012/0184888 A1 | 7/2012 | Alleyne |
| 2012/0215140 A1 | 8/2012 | Hirata et al. |
| 2012/0245491 A1 | 9/2012 | Amell et al. |
| 2013/0015976 A1 | 1/2013 | Chang et al. |
| 2013/0207889 A1 | 8/2013 | Chang et al. |
| 2013/0312168 A1 | 11/2013 | Raanan |
| 2013/0317400 A1 | 11/2013 | Ferezy |
| 2013/0345612 A1 | 12/2013 | Bannister et al. |
| 2014/0009262 A1 | 1/2014 | Robertson et al. |
| 2014/0142485 A1 | 5/2014 | Berry et al. |

OTHER PUBLICATIONS

PCT International Search Report; International App. No. PCT/US2013/075953; Apr. 3, 2014; pp. 1-3.

PCT International Search Report; International App. No. PCT/US2013/075960; Apr. 3, 2014; pp. 1-4.

PCT International Search Report; International App. No. PCT/US2014/036041; Sep. 1, 2014; pp. 1-4.

Itoh, Takaki et al.; "Development of New Instrument for Evaluating Leg Motions Using Acceleration Sensors"; Environmental Health and Preventive Medicine; May 2007; pp. 111-118; vol. 12.

Sander, T. H.; "Magnetoencephalography with a chip-scale atomic magnetometer"; Biomedical Optics Express; May 1, 2012; pp. 981-990; vol. 3; No. 5; Optical Society of America.

U.S. Appl. No. 13/910,511, Hyde et al.
U.S. Appl. No. 13/875,538, Hyde et al.
U.S. Appl. No. 13/748,871, Hyde et al.
U.S. Appl. No. 13/721,474, Hyde et al.

Derawi et al.; "Improved Cycle Detection for Accelerometer Based Gait Authentication"; 2010 Sixth International Conference on Intelligent Information Hiding and Multimedia Signal Processing; 2010; pp. 312-317; 2010 IEEE.

Mannini, Andrea et al.; "Accelerometry-Based Classification of Human Activities Using Markov Modeling"; Computational Intelligence and Neuroscience; accepted Jun. 29, 2011; pp. 1-10; vol. 2011; Hindawi Publishing Corporation.

Middleton, Lee et al.; "A floor sensor system for gait recognition"; School of Electronics and Computer Science, University of Southampton; downloaded on Dec. 21, 2012; 6 pages; United Kingdom.

Rong et al.; "A Wearable Acceleration Sensor System for Gait Recognition"; 2007 Second IEEE Conference on Industrial Electronics and Applications; 2007; pp. 2654-2659; 2007 IEEE.

Sabelman et al.; "Accelerometric Activity Identification for Remote Assessment of Quality of Movement"; Proceedings of the 26$^{th}$ Annual International Conference of the IEEE EMBS; Sep. 1-5, 2004; pp. 4781-4784; 2004 IEEE.

Sekine et al.; "Discrimination of Walking Patterns Using Wavelet-Based Fractal Analysis"; IEEE Transactions on Neural Systems and Rehabilitation Engineering; Sep. 2002; pp. 188-196; vol. 10; No. 3; 2002 IEEE.

Torrealba et al.; "Statistics-based technique for automated detection of gait events from accelerometer signals"; Electronics Letters; Oct. 28, 2010; pp. 1-2; vol. 46; No. 22; The Institution of Engineering and Technology 2010.

PCT International Search Report; International App. No. PCT/US2014/040826; Sep. 22, 2014; pp. 1-3.

\* cited by examiner

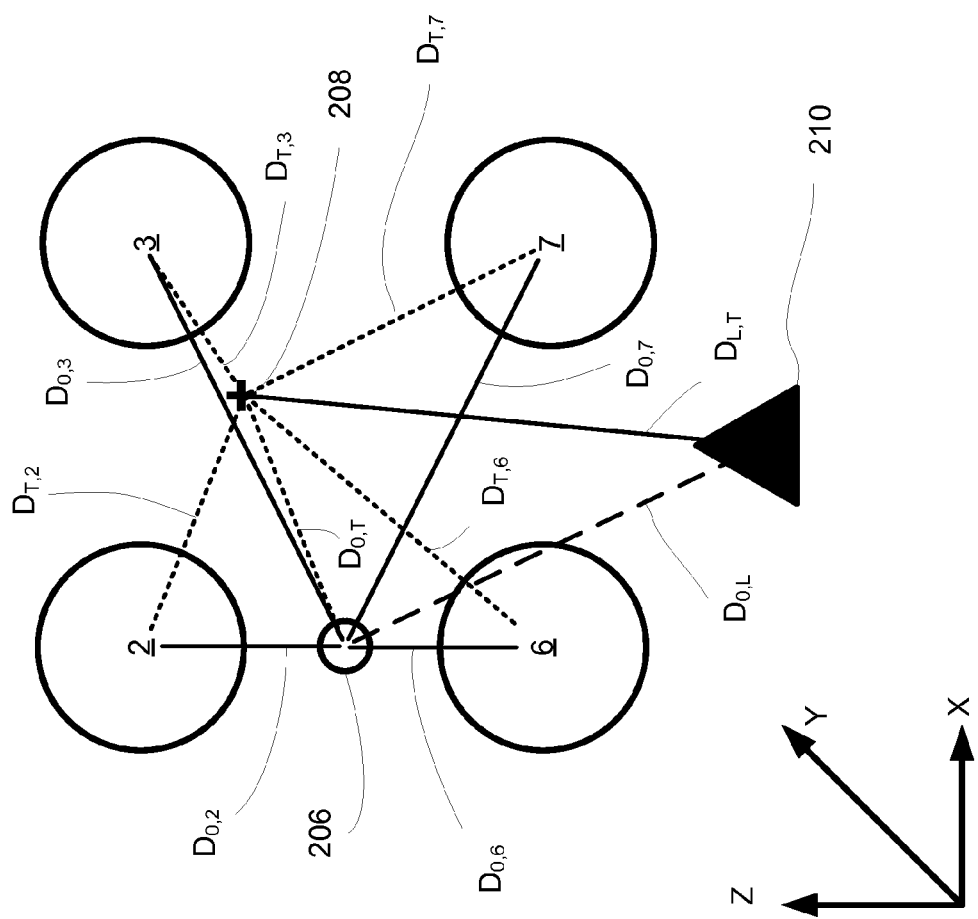
FIG. 3

POSITION SENSING ACTIVE TORSO SUPPORT

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 U.S.C. §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None.

RELATED APPLICATIONS

U.S. patent application Ser. No. 13/721,474, entitled POSTURE DEPENDENT ACTIVE TORSO SUPPORT, naming RODERICK A. HYDE, JORDIN T. KARE, DENNIS J. RIVET, AND LOWELL L. WOOD, Jr. as inventors, filed 20 Dec. 2012, is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

To the extent that the listings of applications provided above may be inconsistent with the listings provided via an ADS, it is the intent of the Application to claim priority to all applications listed in the Priority Applications section of either document.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In one aspect, a method of controlling a torso support includes, but is not limited to receiving a signal indicative of a position of a landmark in or on a body of a subject relative to at least a portion of the torso support worn on the torso of the subject; determining the position of a target region on the torso of the subject relative to the torso support based on the position of the landmark relative to the torso support, the target region having a known position relative to the landmark; selecting at least one force applying element positioned closest to the target region from among a plurality of force applying elements based upon information indicative of the positions of the plurality of force applying elements relative to the torso support; and controlling actuation of the at least one selected force applying element. In addition to the foregoing, other method aspects are described in the claims, drawings, and text forming a part of the disclosure set forth herein.

In one aspect, a torso support includes, but is not limited to, a plurality of force applying elements, each said force applying element adapted to apply force to a localized region of a torso of a subject; at least one positioning element adapted to position the plurality of force applying elements with respect to the torso of the subject, wherein each force applying element is in a known position relative to the torso support; and control circuitry adapted to: receive at least one landmark position signal indicative of a position of a landmark in or on the body of the subject relative to the torso support; determine the position of a target region on the torso of the subject relative to the torso support based on the at least one landmark position signal and on a known position of the target region relative to the landmark; select at least one force applying element positioned closest to the target region; and control actuation of the at least one selected force applying element to apply force to the target region. In addition to the foregoing, other system aspects are described in the claims, drawings, and text forming a part of the disclosure set forth herein.

In one aspect, an article of manufacture includes, but is not limited to, one or more non-transitory machine-readable data storage media bearing one or more instructions for: receiving a signal indicative of a position of a landmark in or on a body of a subject relative to at least a portion of the torso support worn on the torso of the subject; determining the position of a target region on the torso of the subject relative to the torso support based on the position of the landmark relative to the torso support, the target region having a known position relative to the landmark; selecting at least one force applying element positioned closest to the target region from among a plurality of force applying elements based upon information indicative of the positions of the plurality of force applying elements relative to the torso support; and controlling actuation of the at least one selected force applying element. In addition to the foregoing, other aspects of articles of manufacture including one or more non-transitory machine-readable data storage media bearing one or more instructions are described in the claims, drawings, and text forming a part of the disclosure set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

For a more complete understanding of embodiments, reference now is made to the following descriptions taken in connection with the accompanying drawings. The use of the same symbols in different drawings typically indicates similar or identical items, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 3 is an illustration of aspects of selection of force applying elements for applying a force to a target region.

DETAILED DESCRIPTION

Figure 1:
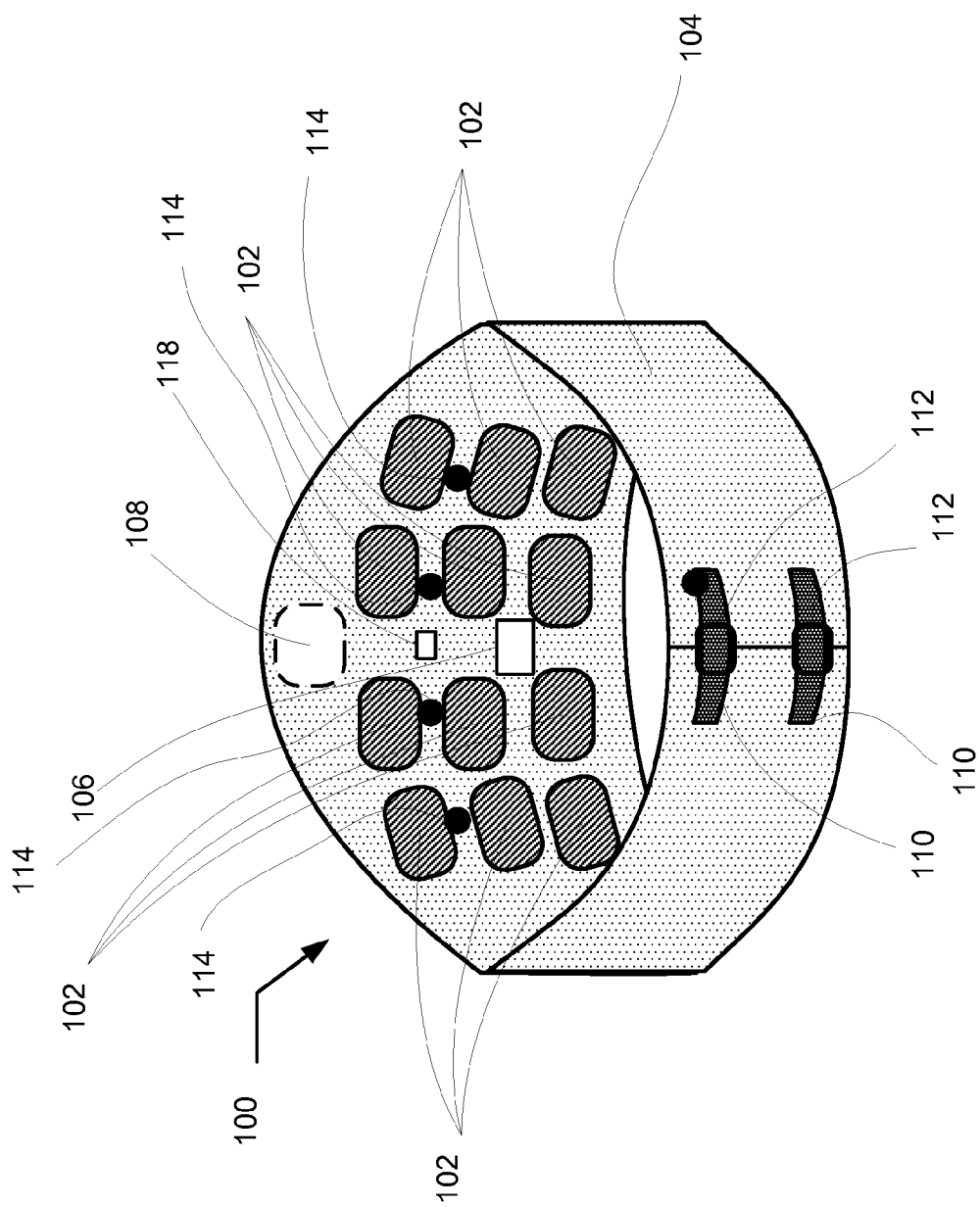
FIG. 1 is an illustration of a torso support.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts a torso support 100, which includes a plurality of force applying elements 102, a positioning element 104, and control circuitry 106. Each force applying element 102 is adapted to apply force to a localized region of a torso of a subject. A force applying element (e.g. force applying element 102 depicted in FIG. 1) can be any structure that is capable of applying force to a region of the torso of the subject. A controllable active force applying element can be controlled by control circuitry 106.

In the embodiment depicted in FIG. 1, force applying elements 102 are expandable fluid/air filled bladders of the type described, for example, in U.S. Pat. No. 4,135,503 to Romano; U.S. Pat. No. 6,540,707 to Stark et al., and U.S. Pat. No. 5,827,209 to Gross et al., each of which is incorporated herein by reference. Expansion of such bladders is controlled through the use of a motorized pump 108 and electrically controlled valves, with feedback provided by pressure sensors (not shown). Force applying elements 102 are fed by fluid lines running from pump 108, which are not depicted in FIG. 1.

Various types of force applying elements can be used in the embodiments described herein. A force applying element can include a torso-contacting portion such as a pad or probe, and a controllable active force applying element that acts to move the torso contacting portion relative to the torso (e.g. by pressing against the torso and/or by applying shear forces to the torso, e.g. by engaging the surface of the torso by friction). For example, in the embodiment shown in FIG. 1, force applying element 102 includes a fabric pad overlying the bladder that serves to distribute the force as well as enhance comfort for the subject. A force applying element may include one or more of an actuator, mechanical linkage, expandable element, inflatable element, pneumatic element, or hydraulic element, or other structures or components capable of applying force or pressure in a controlled fashion to a localized area of the torso. In an aspect, the force applying element includes a passive force applying element and a controllable active force applying element. In an aspect, a force applying element has a controllable stiffness, a controllable dimension, and/or a controllable position relative to the positioning element. The force applying element can include one or more of a spring, an electroactive polymer, an elastic material, or a viscoelastic material. In an aspect, the force applying element includes an actuator, which may include, for example, a mechanical linkage, an expandable element, an inflatable element, a screw, a spring, a magnetic actuator, an electroactive polymer, a pneumatic element, or a hydraulic element. Mechanically or pneumatically driven force applying elements can be, e.g. as described in U.S. Pat. No. 5,624,383 to Hazard et al., which is incorporated herein by reference. Pneumatic and hydraulic piston type force applying elements as described in U.S. Pat. No. 6,746,413 to Reinecke et al., which is incorporated herein by reference, and screw thread/worm gear assembly structures as described in U.S. Published Patent Application 2009/0030359 to Wikenheiser et al., which is incorporated herein by reference, may be positioned to press against the torso (delivering force substantially perpendicular to the skin surface), or positioned to apply shear forces (i.e., force having a significant component parallel to the skin surface). Electromechanical force applying elements having mechanical components driven by electrical control signals, may receive control signals from control circuitry via a wired electrical connection, or via a wireless signal such as an optical or electromagnetic signal transmitted from the control circuitry associated with the force applying element. A force applying element can include a plate (which may be curved or planar), a probe, a post, or any structure having shape and size suitable for applying force to a desired portion of the torso. Force applying elements as used in torso support may be adapted to fit against a region of the torso of the subject, the region of the torso selected from a back, a side, an abdomen, a chest, a ribcage, a stomach, a hip, a pelvic region, a thorax, a shoulder, a buttock, a lower back, and an upper back. In an aspect, at least a portion of the plurality of force applying elements are adapted to apply force to the torso of the subject, such that at least a component of the force is in a direction normal to the surface of the torso of the subject. A force normal to the surface of the torso may be a compressive force or a tensile force. In an aspect, at least a portion of the plurality of force applying elements are adapted to apply force to the torso of the subject, wherein at least a component of the force applied to the torso of the subject is in a direction tangential to the surface of the torso of the subject. A force applying element can also include a skin-engaging element adapted to apply tensile or shear force to the skin surface; for example a skin-engaging element may include an adhesive, a suction cup, a skin penetrating member, a frictional surface, or other components known to those skilled in the art to provide for the application of tensile or shear forces to the skin.

Positioning element 104 is adapted to position the plurality of force applying elements 102 with respect to the torso of the subject, with each force applying element in a known position relative to the torso support. Force applying elements 102, control circuitry 106, pump 108, and other system components described herein are attached to positioning element 104, but in some aspects may be held in place by pressure or friction, e.g. by being pressed between the torso of the subject and the positioning element. Active torso support 100 is configured as a back support or back brace in the example shown in FIG. 1, with positioning element 104 configured as a belt adapted to be fitted around the waist/lower torso of a subject. However, an active torso support may be configured to support or brace other portions of the torso, including, for example, one or more portions of a side, an abdomen, a chest, a ribcage, a stomach, a hip, a pelvic region, a thorax, a shoulder, a buttock, a lower back, and an upper back. In general, a positioning element 104 can be any structure capable of holding force applying element in position with regard to at least a portion of the torso of the subject, and in various embodiments may include, for example, at least one band, strap, belt, or harness, or a garment such as a corset, girdle, jacket, vest, or brief. In various embodiments, the positioning element may include one or multiple straps or other components, without limitation. The positioning element can be constructed from flexible, resilient, or elastic material, including but not limited to leather, fabric, webbing, mesh, cable, cord, flexible metals or polymers, or sections of rigid metals, polymers or other materials connected in such a manner that the sections can be movably fitted around the torso of the subject, e.g. by a hinge or other linkage or by one or more sections of flexible material.

As shown in FIG. 1, positioning element 104 includes fasteners to secure the positioning element with respect to the torso of the subject, e.g. straps 110 and buckles 112 as depicted in FIG. 1. In other embodiments, other types of fasteners as are well known in the art can be used, including but not limited to buckles, snaps, zippers, latches, clips, ties, hook and loop fasteners, lacings, and so forth. A positioning element may include an active or passive tensioning component (for example, elastic) to provide for tightening of the positioning element about the torso of the subject to provide for a secure fit. In an embodiment, a positioning element may simply include an elastic component which allows it to be slid onto the torso of the subject, without the need for fasteners.

It is contemplated that a torso support as described herein functions generally as follows: activation of one or more force applying elements 102 to apply force to a target region of the torso is accomplished by sensing the position of a landmark in or on the torso with respect to the torso support, determining the position of the target region (a muscle or bony structure, for example, to which force is to be applied) relative to the torso support based on at least one signal indicative of a position of a landmark in or on the torso and a known relationship between the landmark and target region, selecting at least one force applying element positioned closest to the target region, and controlling actuation of the at least one selected force applying element to apply force to the target region. In the embodiment of FIG. 1, a plurality of pulse-echo A-mode ultrasound modules 114 (indicated by black circles in FIG. 1) can be used to detect the position of a landmark (e.g., a specific bony structure) on the pelvis, as described in U.S. Patent Publication No. 2010/0198067 to Mahfouze et el., which is incorporated herein by reference.

By selecting the force applying element based upon the sensed position of the landmark, the location at which the force is applied to the torso can be adjusted to compensate for changes in the position of the torso support with respect to the torso of the subject due to different postures or due to movement of the torso support relative to the torso due to, e.g. loosening or slippage of the torso support. If a particular posture and/or motion of a subject is known to produce motion or loading of muscles and/or bony structures in the subject's torso that is likely to result in injury or discomfort, the active torso support can respond to detection of that posture, or motion by applying force to one or more appropriate portions of the torso to provide support expected to prevent or minimize injury or discomfort. For example, in the embodiment of FIG. 1, inclinometer 118 (which can be a MEMS type digital inclinometer (for example, an Analog Devices ADIS16209)) can be used to detect the inclination of the subject's torso, to distinguish between upright and bending postures. The selected force applying element 102 can be activated, for example, when the subject is in a bending posture to provide additional support to the back.

The approach for selecting the force applying element(s) to be activated is described in greater detail in connection with FIGS. 2 and 3.

Figure 2:
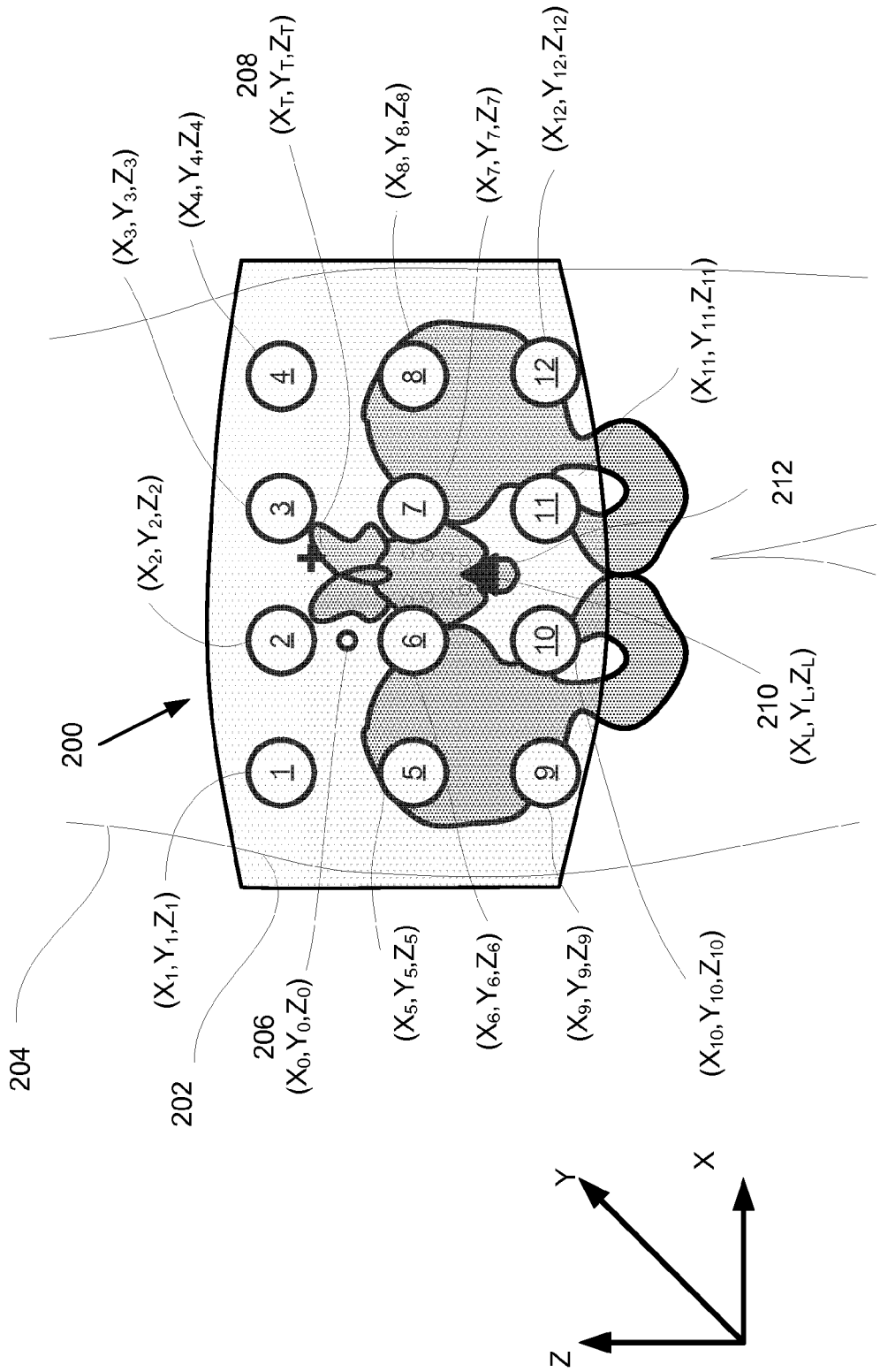
FIG. 2 is an illustration of a torso support.

FIG. 2 depicts a torso support 200, of the type depicted in FIG. 1. Torso support 200 includes multiple force applying elements 1-12 and positioning element 202. Positioning element 202 is configured as a belt worn around the waist/lower torso of subject 204. Positioning element 202 includes a reference location 206, indicated by a white circle in FIG. 2 and having coordinates $X_0$, $Y_0$, $Z_0$. Each of force applying elements 1-12 is attached to positioning element 202 at a known location with respect to reference location 206. Each force applying element i has coordinates $X_i$, $Y_i$, $Z_i$. Also shown are target region 208 (indicated by a cross), having coordinates $X_T$, $Y_T$, $Z_T$, and landmark 210 (indicated by a black triangle), having coordinates $X_L$, $Y_L$, $Z_L$. Target region 208 is a region of the torso of subject 204 at which it is desired to apply force, e.g. to provide support during motion or loading of some or all of the torso. Target region 208 may correspond to a muscle or bony structure, for example. Landmark 210 can be any landmark in or on the torso of the subject that can be sensed by sensors configured to provide a sense signal to the control circuitry of torso support 200. Sensors and control circuitry are not depicted in FIG. 2, but are depicted and described elsewhere herein, for example in connection with FIGS. 1 and 4. In the example shown in FIG. 2, landmark 210 is a region of coccyx 212 of subject 204, which can be distinguished and localized using ultrasound sensors, as discussed in connection with FIG. 1.

FIG. 3 illustrates aspects of the selection of force applying elements for applying force to a target region 208 using torso support 202 as depicted in FIG. 2. FIG. 3 depicts reference location 206, target region 208, and landmark 210 as shown in FIG. 2. For the sake of clarity, only a few of the force applying elements (2, 3, 6 and 7) are shown in FIG. 3. The positions of the various elements of the system shown in FIG. 3 are expressed in Cartesian coordinates, but other coordinate systems may be used. In order to determine which force applying element or elements should be activated to provide force to target region 208, first a signal that contains information regarding the position of the landmark 210 with respect to reference location 206 of the torso support is detected. Various types of signals may be sensed to determine the position of the landmark 210. The position of landmark 210 relative to reference location 206 is indicated by $D_{O,L}$ which may include both scalar and vector components to indicate both distance and direction relative to reference location 206. Next, the position of target region 208 relative to the reference location 206 of the torso support (indicated by $D_{O,T}$) is determined, based on the at least one landmark position signal and on a known position of the target region relative to the landmark (indicated by $D_{L,T}$). In FIG. 3, known positional relationships are indicated by solid lines, measured relationships are indicated by dashed lines, and relationships calculated from other known and/or measured relationships are indicated by dotted lines. As indicated in FIG. 3, $D_{L,T}$ is known, $D_{O,L}$ is measured, and $D_{O,T}$ is determined (calculated) therefrom. At least one force applying element positioned closest to the target region is selected based on the position of each force applying element relative to target region 208. As noted previously, the position of each force applying element is known with respect to the reference position 206 on the positioning element 202. For example, force applying elements 2, 3, 6, and 7 shown in FIG. 3 have known positions ($D_{0,2}$, $D_{0,3}$, $D_{0,6}$, and $D_{0,7}$, respectively) relative to reference location 206. Similarly, other force applying elements 1, 4, 5, and 8-12 shown in FIG. 2 have known positions relative to reference position 206, and the position of each of these force applying elements can thus be determined with respect to target region 208. In an aspect, the positions of all force applying elements with respect to target region 208 can be determined. However, for greater efficiency, once a force applying element having a distance to the target region shorter than the known distance between the force applying elements has been identified, it is not necessary to consider any force applying elements that are more than one such distance away. One or more force applying elements positioned closest to target region 208 can then be selected for activation to apply force to the target region 208. For example the force applying element that is closest to the target region may be selected. "Closest" may refer to the shortest spatial distance, or, in some embodiments, the shortest electrical distance (e.g. lowest impedance/resistance path), or other distance measurement as known to those having skill in the art. In the example shown in FIG. 3, force applying element 3 may be selected as being located at the position closest to target region 208. Once one or more force applying elements have been selected, the selected force applying element(s) can be activated to apply force to the back of the subject. It will be appreciated that, while FIG. 3 depicts a target region that is in a different location than the landmark, in some cases the target region may be in the same location as the landmark (and in some cases the target region itself may serve as the landmark). In such cases, the process for identifying the force applying element(s) to be activated will be simplified in that once the position of the landmark has been determined, no further steps are necessary to determine the position of the target region.

Figure 4:
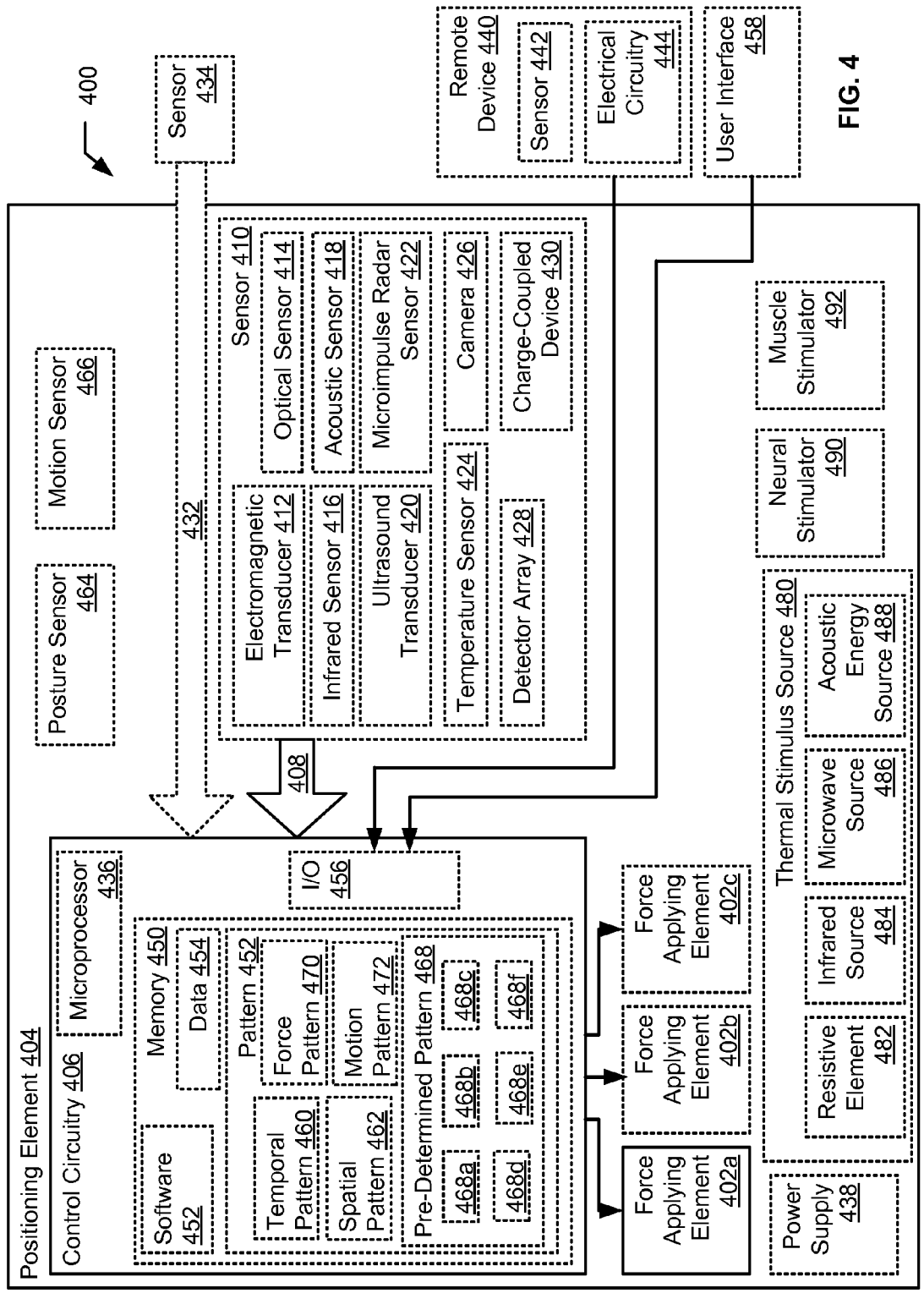
FIG. 4 is a block diagram of a torso support.

FIG. 4 is a block diagram depicting components of a generalized torso support 400, which includes a plurality of force applying elements 402a, 402b, and 402c, a positioning element 404, and control circuitry 406. Force applying elements and positioning elements are as described herein above.

Control circuitry 406 is adapted to receive at least one landmark position signal 408 indicative of a position of a landmark in or on the body of the subject relative to the torso support, determine the position of a target region on the torso of the subject relative to the torso support based on the at least one landmark position signal and on a known position of the target region relative to the landmark, select at least one force applying element (e.g., 402a) positioned closest to the target region, and control actuation of the at least one selected force applying element to apply force to the target region.

In an aspect, the torso support 400 includes at least one sensor 410 adapted to sense a parameter indicative of the position of the landmark in or on the body of the subject and to produce the at least one landmark position signal. The sensor may include, for example, an electromagnetic transducer 412, an optical sensor 414, an infrared sensor 416, an acoustic sensor 418, an ultrasound transducer 420, a micro-impulse radar sensor 422, or a temperature sensor 424. The sensor may be configured to sense muscle activity or neural activity. An electromagnetic sensor (e.g. a surface electrode) may be used for sensing electrical activity produced by a nerve, nerve plexus, or other neural structure, or by a muscle (including cardiac or skeletal muscle) below the skin, as described for example in U.S. Pat. No. 8,170,656 issued May 1, 2012, to Tan et al., which is incorporated herein by reference. Body surface electrical potentials measured with electrodes on the skin surface can be used to determine the location of the heart, e.g. as described in U.S. Pat. No. 7,983,743 issued Jul. 19, 2011 to Rudy et al., which is incorporated herein by reference. Magnetic fields produced by neural activity can be sensed, for example, by a magnetometer, e.g. as described by Sander et al. in "Magnetoencephalography with a chip-scale atomic magnetometer," Biomedical Optics Express, May 2012, Vol. 3, No. 5, p. 982, which is incorporated herein by reference.

In an aspect, infrared sensing is used for imaging blood vessels to map the vasculature in the torso of the subject, using a method as described in U.S. Pat. No. 8,238,622 issued Aug. 7, 2012 to Miura et al. See also U.S. Pat. No. 4,032,889 to Nassimbene issued Jun. 28, 1977, which is incorporated herein by reference. U.S. Pat. No. 8,229,178 issued Jul. 24, 2012 to Zhang et al., which is incorporated herein by reference, describes a method for acquiring a palm vein image with visible and infrared light and extracting features from the image for authentication of individual identity. It will be appreciated that the feature extraction and template matching approach used to authenticate identity could similarly be used to match a detected image with a map to localize a landmark.

The sensor may include a camera 426, a detector array 428 (which may be linear array, or two-dimensional array, for example), or Charge-Coupled Device (CCD) 430. In an aspect, the landmark can be a feature on the skin surface such as a pore, a mole, a wrinkle, a hair shaft or hair follicle, etc. Skin characteristics can be identified in an image obtained with CCD sensor, and compared to a reference image to determine a landmark location, using an approach as described in U.S. Pat. No. 7,697,735 issued Apr. 13, 2010 to Adam et al., which is incorporated herein by reference. Registration and comparison of biometric data with template date can be performed as described, for example, in U.S. Pat. No. 8,264,325 issued Sep. 11, 2012 to Fukuda et al., which is incorporated herein by reference.

Acoustic sensors (particularly ultrasound) can be used to detect bony and/or soft-tissue structures within the torso of the subject, using a system and approach generally as described in U.S. Published Application No. 2010/0198067 to Mahfouze et el., dated Aug. 5, 2010, which is incorporated herein by reference.

In an aspect, micro-impulse radar sensors can be used to detect air or fluid filled regions within the torso, which may serve as landmarks in some embodiments, as described in U.S. Pat. No. 6,233,479 issued May 15, 2001 to Haddad et al., which is incorporated herein by reference. Cardiac and neural activity may be detected with a 10 GHz probe, as discussed in U.S. Pat. No. 4,344,440 issued Aug. 17, 1982 to Aaby et al.

In an aspect, a sensor includes a temperature sensor. Temperature sensors are well known to those having skill in the art, including but not limited to resistance temperature detectors (e.g., thermistors, thin film temperature sensors), thermocouples, and infrared/pyroelectric thermometers, etc. Temperature measurements may provide information about muscle damage, inflammation, blood flow, for example.

In an aspect, torso support 400 receives a landmark position signal 432 from a remote sensor 434 not located on the torso support. The transmission of signals from remote sensors to control circuitry on the torso support can occur over a wireless link, as is well known in the art, for example, as described in U.S. Pat. No. 8,170,656 issued May 1, 2012, to Tan et al., and U.S. Published Application No. 2010/0198067 to Mahfouze et el., dated Aug. 5, 2010, each of which is incorporated herein by reference. For example in an aspect a signal from a remote video camera can supply information regarding the position of a landmark.

Control circuitry 406 may include analog or digital electrical circuitry. In an aspect, control circuitry 406 may include a microprocessor 436. Torso support 400 may include various other elements, including power supply 438. Torso support 400 may be used in connection with a remote device 440, which may include one or more sensors 442, as well as electrical circuitry 444. Control circuitry 406 may include memory 450, which may store software (program modules) 452 used in the operation of torso support 400, and/or data 454. Control circuitry 406 may include I/O structure 456, which provides for communication with remote device 440, e.g. via a wired or wireless (e.g. electromagnetic or optical) connection, or with a user interface 458. Electrical circuitry 444 in remote device 440 includes any electrical circuitry needed for processing signal from sensors 442 and sending signals to or receiving signals from active torso support 400 via I/O structure 456.

In an aspect, the control circuitry 406 is adapted to control actuation of the at least one selected force applying element according to a temporal pattern 460. In an aspect, the control circuitry is adapted to select at least one additional force applying element (e.g. 402b and/or 402c), and to control actuation of the at least one selected force applying element 402a and the at least one additional force applying element (402b and/or 402c) according to a spatial pattern 462 and temporal pattern 460. For example, a spatial pattern provides for applying force at several spatially separated locations to support several different muscles (or different portions of a larger muscle) that are loaded or stressed during a particular motion. Controlling actuation according to a temporal pattern may be as simple as applying a constant force at a selected location for a specific duration (e.g., a duration corresponding to an expected duration of a particular motion, such as a portion of a gait cycle), or applying a force that gradually ramps up to a maximum value as a function of time. More complex temporal or spatio-temporal patterns (e.g. cyclical patterns) may also be employed.

In an aspect, control of the torso support is based upon sensed motion or posture of the subject. Thus, in an aspect, torso support includes at least one sensor 464 adapted for sensing a posture of the subject, and/or at least one sensor 466 adapted for sensing a motion of the subject. Sensor 464 for sensing posture of the subject may include, for example an integrating accelerometer or an inclinometer. Posture sensing may be performed, for example, as described in U.S. patent application Ser. No. 13/721,474, entitled Posture Dependent Active Torso Support, naming Roderick A. Hyde, Jordin T. Kare, Dennis J. Rivet, and Lowell L. Wood, Jr. as inventors, filed 20 Dec. 2012, which is incorporated herein by reference.

A sensor 466 for sensing motion of the subject may include various types of motion sensors known to those having skill in the art, examples of which include a sensor system as described in U.S. Published Patent Application 2011/0082393, to Bort, dated Apr. 7, 2011, which employs piezoelectric sensors to detect deformation of an orthosis caused by movements of a body region, which is incorporated herein by reference; accelerometers, strain gauges, and pressure gauges as described in U.S. Published Patent Application 2001/0020143 to Stark et al., dated Sep. 6, 2001, which is incorporated herein by reference; and force and pressure sensors for detecting joint motion and stress, as discussed in U.S. Pat. No. 5,827,209 issued Oct. 27, 1998 to Gross, which is incorporated herein by reference.

A signal from sensor 464 or sensor 466 may be processed by control circuitry to determine the posture or motion of the subject. Control circuitry 406 may be configured to cause the application of force to a particular target location (e.g. a weak muscle in the subject's back) upon detection of a motion anticipated to cause loading or strain on the muscle. For example, the torso support could be activated to apply force to the weak muscle upon detection of a motion corresponding to the subject bending to pick up an object from the floor, and to release the support once the subject had straightened up again.

Control circuitry 406 may be adapted to control actuation of the at least one selected force applying element (e.g. 402a) according to a pre-defined pattern 468 selectable from a plurality of pre-defined patterns (e.g. 468a-468f). For example, the torso support 400 may include a user input (e.g., user interface 458 may be a user input), and pre-defined pattern 468 may be selectable from the plurality of pre-defined patterns 468a-468f based upon an input received on the user input 458. Alternatively, or in addition, the torso support 400 may include at least one sensor 464 or 466, adapted for sensing a motion or posture of the subject, respectively, as described herein above, and pre-defined pattern 468 may be selectable from the plurality of pre-defined patterns 468a-468f based upon a sensed motion or posture of the subject. In an aspect, the plurality of pre-defined patterns 468a-468f includes patterns corresponding to a plurality of pre-defined motions or postures of the subject, which may include, but is not limited to, standing, sitting, lying, walking, getting up, sitting down, lying down, twisting, leaning forward, or rolling while lying down (e.g., changing position from lying on a back to lying on a side, lying on a side to lying on a front, lying on a side to lying on a back, lying on a front to lying on a side, and so forth). Control circuitry 406 may be adapted to control actuation of the at least one selected force applying element 402a by controlling a pattern of force applied by the at least one selected force applying element 402a, or by controlling a pattern of motion generated by the at least one selected force applying element 402a, for example by using force pattern 470 or motion pattern 472.

In an embodiment, torso support includes a thermal stimulus source 480, which may include for example, a resistive element 482, an infrared source 484, a microwave source 486, an acoustic energy source 488, or other elements capable of providing localized heating to the skin or underlying tissues. A thermal stimulus may be applied to stimulate blood circulation, promote healing, enhance comfort of sore or injured muscles, or serve as a counter-stimulus to reduce sensation of pain, for example.

In an embodiment, the torso support includes a neural stimulator 490 or a muscle stimulator 492. A neural stimulator 490 or muscle stimulator 492 may include an electrode for delivering an electrical stimulus, or one or more coils for delivering a magnetic stimulus, for example, either of which can be driven by an appropriately configured electrical control signal, as known to those having skill in the art. (See, for example, U.S. Pat. No. 8,285,381 issued Oct. 9, 2012 to Fahey et al., which is incorporated herein by reference). Other types of neural or muscle stimulators may be used, as known to those having skill in the art. Nerve and/or muscle stimulation can be used to activate muscles to provide a higher level of strength or stability in the back, or to block or counter pain signals, for example.

In a general sense, those skilled in the art will recognize that the various embodiments described herein can be implemented, individually and/or collectively, by various types of electrical circuitry having a wide range of electrical components such as hardware, software, firmware, and/or virtually any combination thereof, limited to patentable subject matter under 35 U.S.C. §101. Electrical circuitry (e.g., control circuitry 406 and electrical circuitry 444 depicted in FIG. 4) includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). In a general sense, those skilled in the art will recognize that the various aspects described herein which can be implemented, individually and/or collectively, by a wide range of hardware, software, firmware, and/or any combination thereof can be viewed as being composed of various types of "electrical circuitry."

Those skilled in the art will recognize that at least a portion of the devices and/or processes described herein can be integrated into a data processing system. Those having skill in the art will recognize that a data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Figure 5:
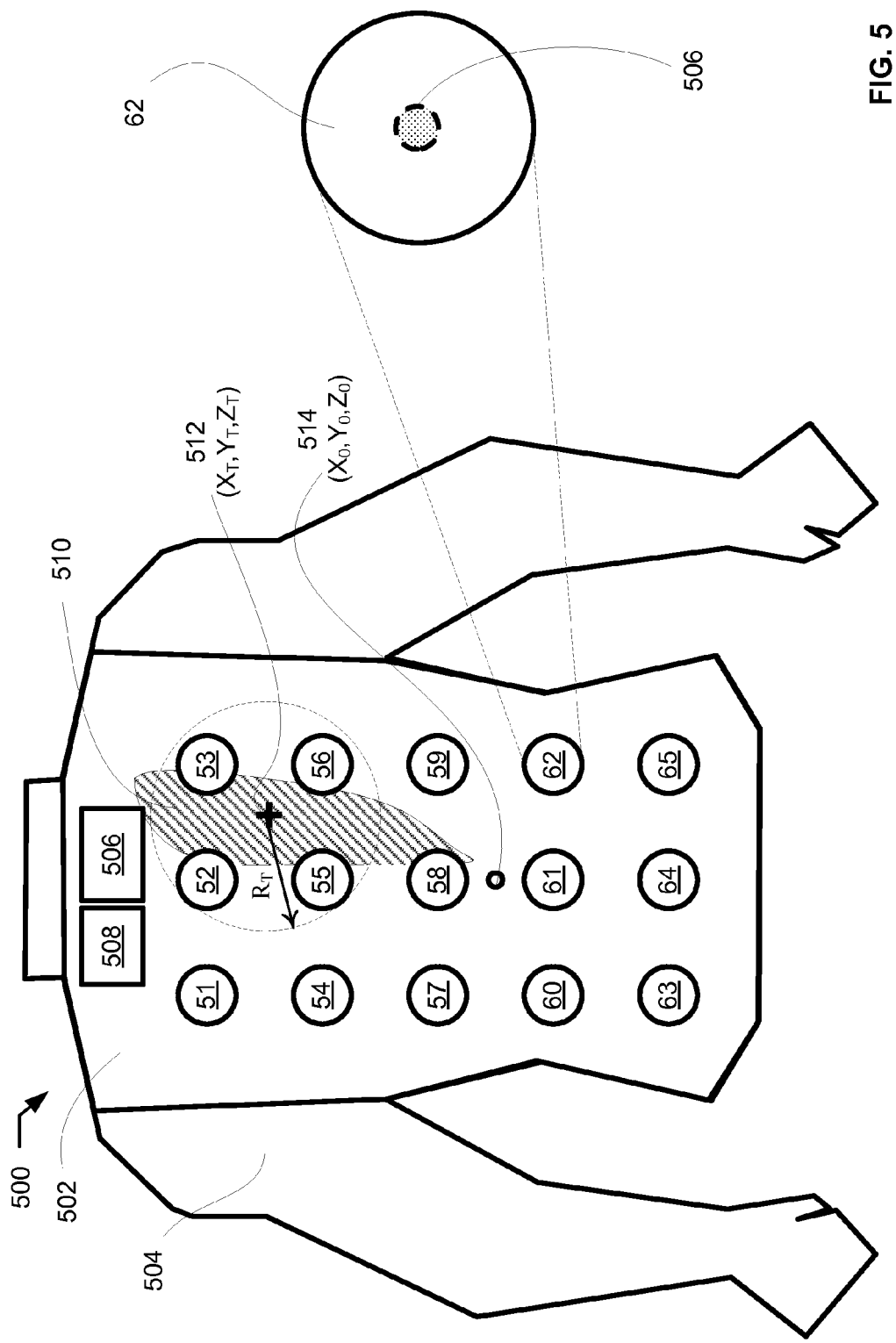
FIG. 5 is an illustration of a torso support.

A further example of a torso support is depicted in FIG. 5. In this example, the sensed landmark, as well as the target region to which force is applied is an active muscle; thus the landmark and the target region are co-located and have the same position relative to the torso support. Torso support 500 includes positioning element 502, which is configured as a vest worn on the torso of subject 504, a plurality of electromechanical force applying elements 51-65, control circuitry 506, and power supply 508, which may be, for example a battery, housed with or adjacent to control circuitry 506. Control circuitry 506 is connected to force applying elements 51-65 by wired connections (not shown). However, as an alternative, control circuitry 506 and force applying elements 51-65 could include transmitters and receivers for wireless communication between components. Each of force applying elements 51-65 has associated therewith an electrical sensor (e.g., an electrode) adapted to contact the skin of the subject to detect electrical activity (electromyogram, or EMG) associated with muscle activity. See, for example, electrode 506 on force applying element 62, illustrated in expanded view. Electrode 506 is located on the side of force applying element 62 that faces toward the torso of subject 504 so that it can contact the skin of subject 504. In use, electrical activity from a muscle (e.g. muscle 510) is sensed from one or more electrodes associated with force applying elements. For example, activity from muscle 510 would produce an EMG signal detectable by electrodes associated with force applying elements 52, 53, 55, 56 and 58. The position of active muscle 510 is determined based on the EMG signal levels on the various electrodes. Thus, a combined landmark/target region 512 having location $(X_T, Y_T, Z_T)$ relative to reference point 514 on torso support 500, corresponding to a central region of muscle 510, is identified. Accordingly one or more force applying elements are selected to apply force to the target region. For example, force applying elements 52, 53, 55 and 56 may be selected as being within a radius $R_T$ of target region 512. Selected force applying elements 52, 53, 55 and 56 can then be actuated to deliver force to target region 512. In an aspect, force applying elements 52, 53, 55 and 56 can be actuated to deliver force to target region 512 while muscle 510 is actively contracting. In another aspect, force applying elements 52, 53, 55 and 56 can be actuated to deliver force to target region 512 at a specified delay following active contraction of muscle 510.

Figure 6:
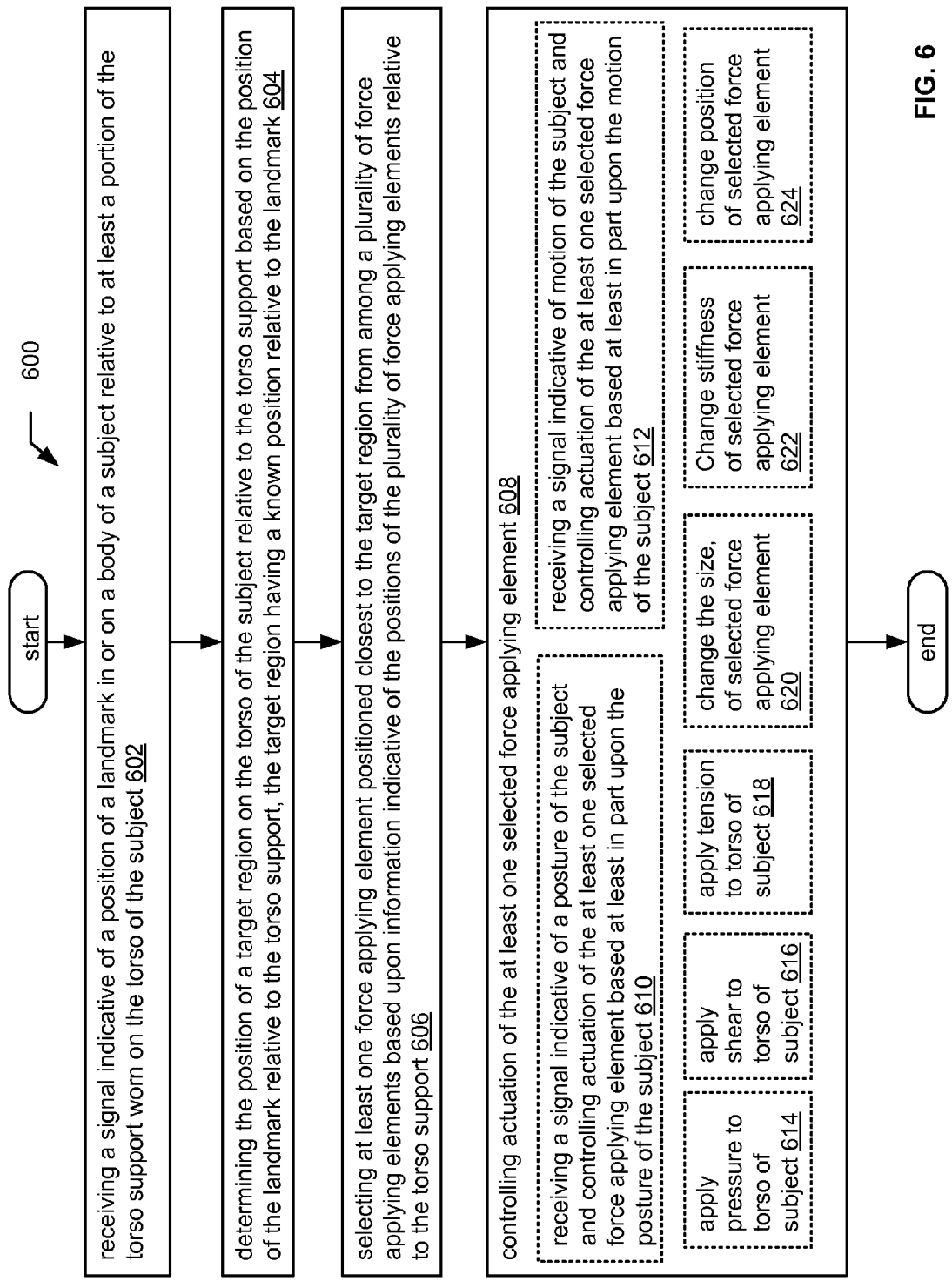
FIG. 6 is a flow diagram of a method of controlling a torso support.

FIG. 6 is a flow diagram of a method 600 of controlling a torso support as described herein. Method 600 includes receiving a signal indicative of a position of a landmark in or on a body of a subject relative to at least a portion of a torso support worn on the torso of the subject, as indicated at 602; determining the position of a target region on the torso of the subject relative to the torso support based on the position of the landmark relative to the torso support, the target region having a known position relative to the landmark, at 604; selecting at least one force applying element positioned closest to the target region from among a plurality of force applying elements based upon information indicative of the positions of the plurality of force applying elements relative to the torso support, at 606; and controlling actuation of the at least one selected force applying element, at 608.

In an aspect, method 600 also includes receiving a signal indicative of a posture of the subject and controlling actuation of the at least one selected force applying element based at least in part upon the posture of the subject, as indicated at 610. In an aspect, the method includes receiving a signal indicative of motion of the subject and controlling actuation of the at least one selected force applying element based at least in part upon the motion of the subject, as indicated at 612.

In an aspect, method 600 includes controlling actuation of the at least one selected force applying element to apply pressure 614, shear 616, or tension 618 to the torso of the subject. The method can include controlling actuation of the at least one selected force applying element to change the size 620, stiffness 622, or position 624 of the at least one selected force applying element.

Figure 7:
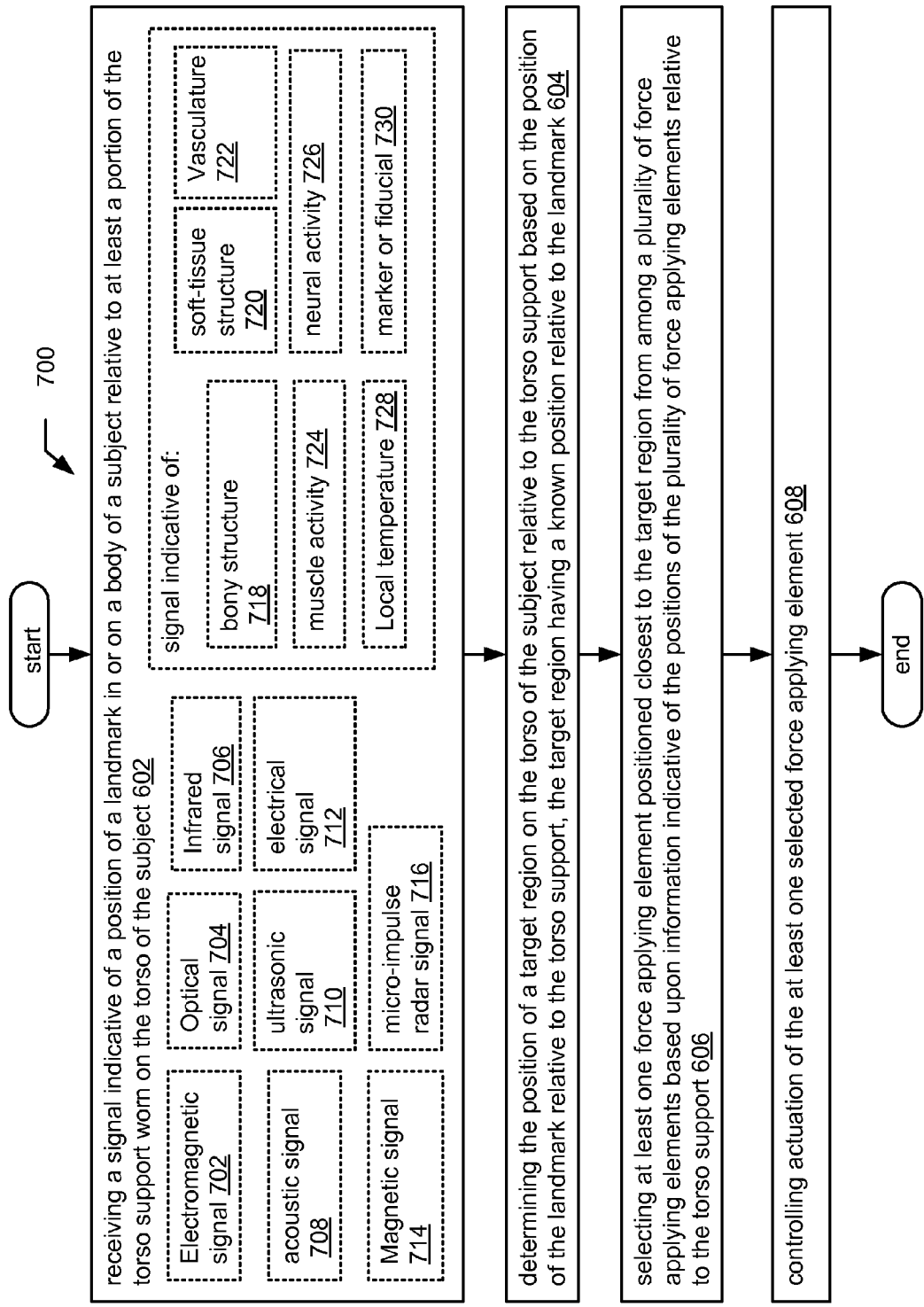
FIG. 7 is a flow diagram of a method of controlling a torso support.

FIG. 7 depicts a method 700, including variations of the method shown in FIG. 6. In various embodiments, receiving a signal indicative of a position of a landmark includes receiving an electromagnetic signal 702, optical signal 704, infrared signal 706, acoustic signal 708, ultrasonic signal 710, electrical signal 712, magnetic signal 714, or micro-impulse radar signal 716. Receiving a signal indicative of the position of a landmark may include receiving a signal indicative of at least one bony structure within the body of the subject 718, a soft-tissue structure within the body of the subject 720, vasculature below a skin surface of the body of the subject 722, muscle activity 724, neural activity 726, or a local temperature 728 on or below the skin surface. Receiving a signal indicative of the position of a landmark may include receiving a signal indicative of a marker or fiducial 730, which may be on the skin surface of the subject, or below the skin surface of the subject.

Figure 8:
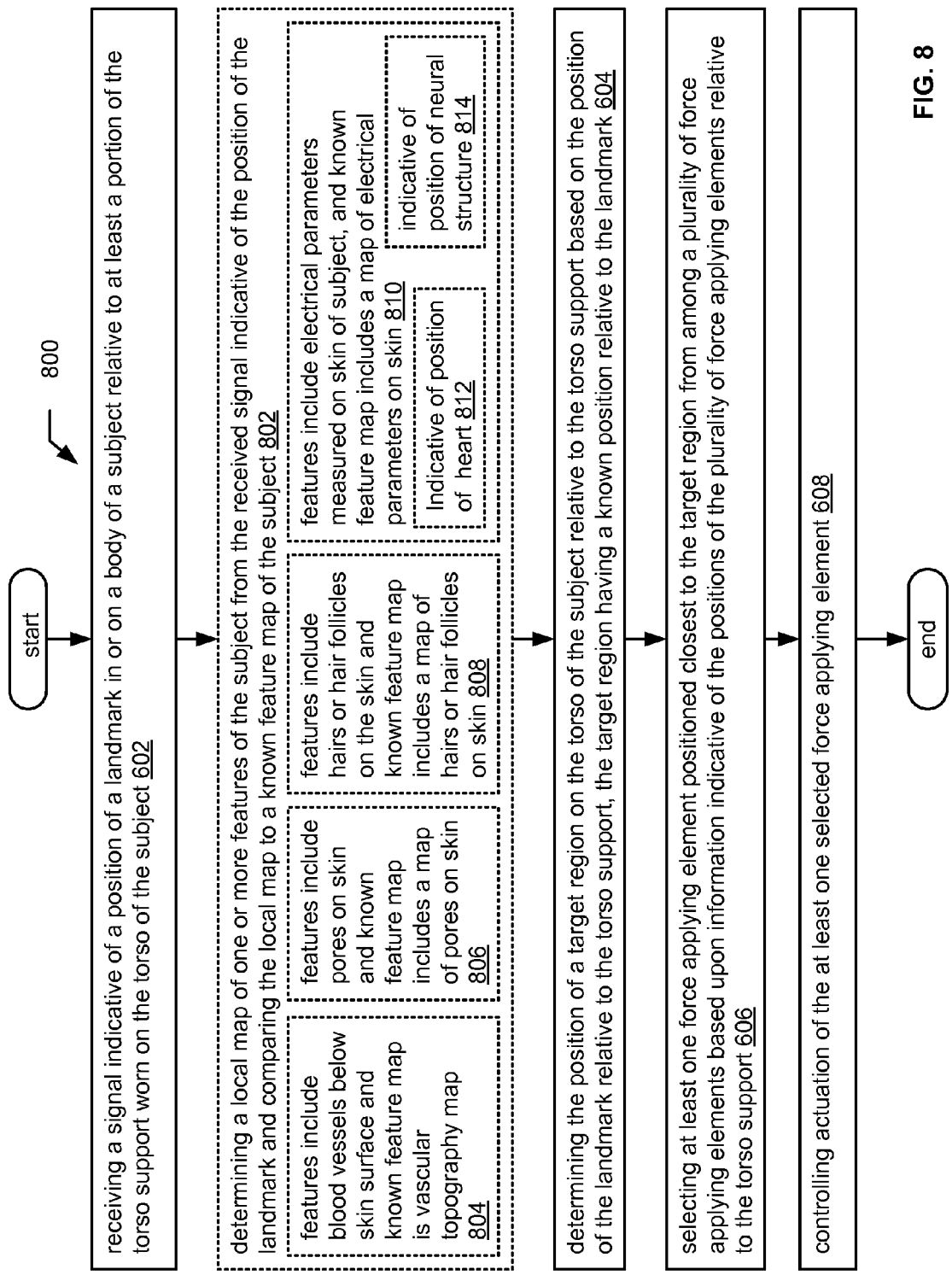
FIG. 8 is a flow diagram of a method of controlling a torso support.

As shown in FIG. 8, in an aspect, a related method 800 includes determining a local map of one or more features of the subject from the received signal indicative of the position of the landmark and comparing the local map to a known feature map of the subject, as indicated at 802. For example, in an aspect the one or more features include blood vessels below a skin surface of the body of the subject, and the known feature map is a vascular topography map of the subject, as indicated at 804. In another aspect, the one or more features include pores on the skin of the subject, and the known feature map includes a map of pores on the skin of the subject, as indicated at 806. In another aspect, the one or more features include hairs or hair follicles on the skin of the subject, and the known feature map includes a map of hairs or hair follicles on the skin of the subject, as indicated at 808. In an aspect, the one or more features include electrical parameters measured on the skin of the subject, and the known feature map includes a map of electrical parameters on the skin of the subject, as indicated at 810. The electrical parameters may be indicative of the position of the heart of the subject, as indicated at 812 or the position of a neural structure of the subject, as indicated at 814, for example.

In various embodiments, methods as described herein may be performed according to instructions implementable in hardware, software, and/or firmware. Such instructions may be stored in non-transitory machine-readable data storage media, for example. Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 U.S.C. §101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware. In some implementations described herein, logic and similar implementations may include software or other control structures. Electrical circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof, limited to patentable subject matter under 35 U.S.C.

§101. In an embodiment, several portions of the subject matter described herein may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. §101, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may also include transmission type medium such as a digital and/or an analog communication medium (e.g., a fiber optic cable, a waveguide, a wired communications link, a wireless communication link (e.g., transmitter, receiver, transmission logic, reception logic, etc.) and so forth).

Figure 9:
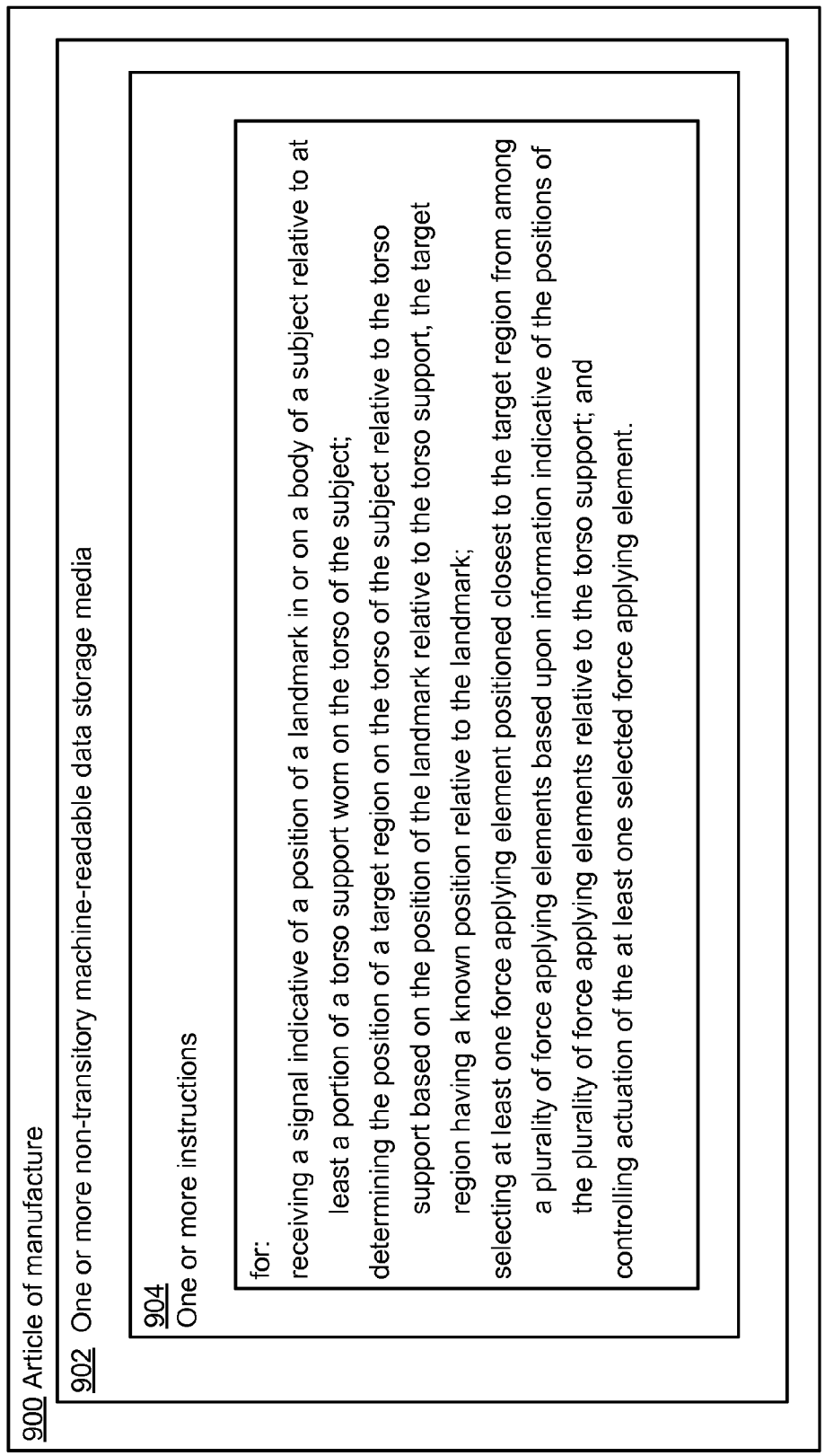
FIG. 9 illustrates an article of manufacture including non-transitory machine-readable data storage media bearing one or more instructions.

FIG. 9 depicts an article of manufacture 900 that includes one or more non-transitory machine-readable data storage media 902 bearing one or more instructions 904 for: receiving a signal indicative of a position of a landmark in or on a body of a subject relative to at least a portion of the torso support worn on the torso of the subject; determining the position of a target region on the torso of the subject relative to the torso support based on the position of the landmark relative to the torso support, the target region having a known position relative to the landmark; selecting at least one force applying element positioned closest to the target region from among a plurality of force applying elements based upon information indicative of the positions of the plurality of force applying elements relative to the torso support; and controlling actuation of the at least one selected force applying element. Instructions 904 depicted in FIG. 9 correspond to the method 600 shown in FIG. 6. Other variants of methods as depicted in FIGS. 6-8 and as described herein can be implemented through the use of non-transitory machine-readable data storage media bearing one or more suitable instructions.

In an aspect, the one or more non-transitory machine readable data storage media 902 bear one or more instructions 904 for receiving a signal indicative of a posture of the subject and controlling actuation of the at least one selected force applying element based at least in part upon the posture of the subject. In an aspect, the one or more non-transitory machine readable data storage media 902 bear one or more instructions 904 for receiving a signal indicative of motion of the subject and controlling actuation of the at least one selected force applying element based at least in part upon the motion of the subject.

The one or more non-transitory machine readable data storage media 902 may bear one or more instructions 904 for determining the position of at least one bony structure within the body of the subject, a soft-tissue structure within the body of the subject, vasculature below a skin surface of the body of the subject, an active muscle, or an active neural structure.

The one or more non-transitory machine readable data storage media 902 may bear one or more instructions 904 for determining the position of the target region based upon one or measurements of local temperature on or below the skin surface.

The one or more non-transitory machine readable data storage media 902 may bear one or more instructions 904 for determining the position of a marker or fiducial on the skin surface of the subject, or below the skin surface of the subject.

The one or more non-transitory machine readable data storage media 902 may bear one or more instructions 904 for determining a local map of one or more features of the subject from the received signal indicative of the position of the landmark and one or more instructions 904 for comparing the local map to a known feature map of the subject. For example, in various embodiment, the one or more features include blood vessels below a skin surface of the body of the subject and the known feature map is a vascular topography map of the subject; the one or more features include pores on the skin of the subject and the known feature map includes a map of pores on the skin of the subject; the one or more features include hairs or hair follicles on the skin of the subject and the known feature map includes a map of hairs or hair follicles on the skin of the subject; or the one or more features include electrical parameters measured on the skin of the subject, and the known feature map includes a map of electrical parameters on the skin of the subject. Electrical parameters may be indicative of the position of the heart of the subject, or the position of a neural structure (such as a nerve, spinal cord, nerve ganglion, nerve plexus, etc.) of the subject.

In an aspect, the one or more non-transitory machine readable data storage media 902 bear one or more instructions 904 for controlling actuation of the at least one selected force applying element to apply pressure, shear, or tension to the torso of the subject.

In an aspect, the one or more non-transitory machine readable data storage media 902 bear one or more instructions 904 for controlling actuation of the at least one selected force applying element, for example, to change the size, stiffness, or position of the at least one selected force applying element.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A torso support comprising:
   a plurality of force applying elements, each said force applying element configured to apply force to a localized region of a torso of a subject;
   at least one positioning element configured to position the plurality of force applying elements with respect to the torso of the subject, wherein each force applying element is in a known position relative to the torso support; and
   a control circuitry including
      electrical circuitry for receiving from at least one sensor at least one landmark position signal indicative of a position of a landmark in or on a body of the subject relative to the torso support;
      signal processing circuitry for calculating the position of a target region on the torso of the subject relative to the torso support based on the at least one landmark position signal and on a known position of the target region relative to the landmark;
      signal processing circuitry for selecting at least one force applying element positioned closest to the target region; and
      electrical circuitry for generating an electrical control signal for controlling actuation of the at least one selected force applying element to apply force to the target region.

2. The torso support of claim 1, comprising at least one sensor configured to sense a parameter indicative of the position of the landmark in or on the body of the subject and to produce the at least one landmark position signal.

3. The torso support of claim 2, wherein the at least one sensor includes at least one of an electromagnetic transducer, an optical sensor, an infrared sensor, an acoustic sensor, an ultrasound transducer, a micro-impulse radar sensor, a temperature sensor, a sensor configured to sense muscle activity, a sensor configured to sense neural activity, a camera, a detector array, and a charge-coupled device.

4. The torso support of claim 1, wherein at least one of the force applying elements includes an actuator.

5. The torso support of claim 4, wherein the actuator includes at least one of a mechanical linkage, a piezoelectric actuator, a thermally responsive element, an expandable element, an inflatable element, a screw, a spring, a magnetic actuator, an electroactive polymer, a pneumatic element, and a hydraulic element.

6. The torso support of claim 1, wherein the control circuitry is configured to control actuation of the at least one selected force applying element according to a temporal pattern.

7. The torso support of claim 1, wherein the control circuitry is configured to select at least one additional force applying element, and to control actuation of the at least one selected force applying element positioned closest to the target region and at least one additional force applying element according to a spatial and temporal pattern.

8. The torso support of claim 1, wherein the control circuitry is configured to control actuation of the at least one selected force applying element according to a pre-defined pattern selectable from a plurality of pre-defined patterns.

9. The torso support of claim 1, wherein at least a portion of the plurality of force applying elements are configured to apply force to the torso of the subject, wherein at least a component of the force is in a direction normal to a surface of the torso of the subject.

10. The torso support of claim 1, wherein at least a portion of the plurality of force applying elements are configured to apply force to the torso of the subject, wherein at least a component of the force applied to the torso of the subject is in a direction tangential to a surface of the torso of the subject.

11. The torso support of claim 1, wherein the at least one selected force applying element includes at least one of a plate, a probe, a post, a skin-engaging element adapted to apply tensile or shear force to a skin surface, a spring, an electroactive polymer, an elastic material, and a viscoelastic material.

12. The torso support of claim 1, wherein the at least one selected force applying element has at least one of a controllable stiffness, a controllable dimension, and a controllable position relative to the positioning element.

13. The torso support of claim 1, wherein the control circuitry includes at least one of a microprocessor, software, analog electronic circuitry and digital electronic circuitry.

14. The torso support of claim 1, comprising at least one sensor adapted for sensing at least one of a posture of the subject and a motion of the subject.

15. The torso support of claim 1, wherein the control circuitry is configured to control actuation of the at least one selected force applying element by controlling at least one of a pattern of force applied by the at least one selected force applying element and a pattern of motion generated by the at least one selected force applying element.

16. The torso support of claim 1, comprising at least one of a thermal stimulus source, a neural stimulator, and a muscle stimulator.

17. A method of controlling a torso support comprising:
receiving with electrical circuitry at least one landmark position signal from at least one sensor, the at least one landmark position signal indicative of a position of a landmark in or on a body of a subject relative to at least a portion of the torso support worn on the torso of the subject, the torso support including
a plurality of force applying elements, each said force applying element configured to apply force to a localized region of the torso of a subject;
at least one positioning element configured to position the plurality of force applying elements with respect to the torso of the subject, wherein each force applying element is in a known position relative to the torso support; and
a control circuitry including
the electrical circuitry for receiving from the at least one sensor the at least one landmark position signal indicative of a position of a landmark in or on a body of the subject relative to the torso support;
signal processing circuitry for calculating the position of a target region on the torso of the subject relative to the torso support based on the at least one landmark position signal and on a known position of the target region relative to the landmark;
signal processing circuitry for selecting at least one force applying element positioned closest to the target region; and
electrical circuitry for generating an electrical control signal for controlling actuation of the at least one selected force applying element to apply force to the target region;
determining the position of a target region on the torso of the subject relative to the torso support based on the position of the landmark relative to the torso support with the signal processing circuitry for calculating the position of the target region;
selecting at least one force applying element positioned closest to the target region from among a plurality of force applying elements based upon information indicative of the positions of the plurality of force applying elements relative to the torso support with the signal processing circuitry for selecting the at least one force applying element; and
controlling actuation of the at least one selected force applying element by generating the electrical control signal with the electrical circuitry for generating the electrical control signal.

18. The method of claim 17, comprising determining a local map of one or more features of the subject from the landmark position signal indicative of the position of the landmark and comparing the local map to a known feature map of the subject.

19. The method of claim 18, wherein the one or more features include electrical parameters measured on a skin of the subject, and wherein the known feature map includes a map of electrical parameters on the skin of the subject.

20. The method of claim 19, wherein the electrical parameters are indicative of at least one of the position of a heart of the subject and the position of a neural structure of the subject.

21. The method of claim 18, wherein the one or more features include blood vessels below a skin surface of the body of the subject, and wherein the known feature map is a vascular topography map of the subject.

22. The method of claim 18, wherein the one or more features include pores on a skin of the subject, and wherein the known feature map includes a map of pores on the skin of the subject.

23. The method of claim 18, wherein the one or more features include hairs or hair follicles on a skin of the subject, and wherein the known feature map includes a map of hairs or hair follicles on the skin of the subject.

24. The method of claim 17, wherein the position of the target region is the same as the position of the landmark.

25. The method of claim 17, wherein the position of the target region is different from the position of the landmark.

26. The method of claim 17, comprising at least one of receiving a signal indicative of a posture of the subject and controlling actuation of the at least one selected force applying element based at least in part upon the posture of the subject and receiving a signal indicative of motion of the subject and controlling actuation of the at least one selected force applying element based at least in part upon the motion of the subject.

27. The method of claim 17, wherein receiving a signal indicative of a position of a landmark includes receiving at least one of an electromagnetic signal, an optical signal, an infrared signal, an acoustic signal, an ultrasonic signal, an electrical signal, a magnetic signal, and a micro-impulse radar signal.

28. The method of claim 17, wherein receiving a signal indicative of a position of a landmark includes receiving a signal indicative of at least one of a bony structure within the body of the subject, a soft-tissue structure within the body of the subject, vasculature below a skin surface of the body of the subject, muscle activity, neural activity, a local temperature on or below the skin surface, a marker or fiducial on the skin surface of the subject, and a marker or fiducial below the skin surface of the subject.

29. The method of claim 17, including controlling actuation of the at least one selected force applying element to apply at least one of pressure, shear, and tension to the torso of the subject.

30. The method of claim 17, including controlling actuation of the at least one selected force applying element to change at least one of a size, a stiffness, and the position of the at least one selected force applying element.

* * * * *